(12) United States Patent
Kim et al.

(10) Patent No.: US 11,365,396 B2
(45) Date of Patent: Jun. 21, 2022

(54) IN VITRO FIBROSIS MODEL, PREPARING METHOD THEREFOR, AND USE THEREOF

(71) Applicant: S-BIOMEDICS, Seoul (KR)

(72) Inventors: Sang Heon Kim, Seoul (KR); Kwi Deok Park, Seoul (KR); Kang Won Lee, Seoul (KR); Thanavel Rajangam, Seoul (KR)

(73) Assignee: S-BIOMEDICS, Seoul (KR)

( * ) Notice: Subject to any disclaimer, the term of this patent is extended or adjusted under 35 U.S.C. 154(b) by 287 days.

(21) Appl. No.: 16/678,014

(22) Filed: Nov. 8, 2019

(65) Prior Publication Data

US 2020/0071674 A1  Mar. 5, 2020

Related U.S. Application Data

(62) Division of application No. 15/551,595, filed as application No. PCT/KR2016/005501 on May 25, 2016, now abandoned.

(30) Foreign Application Priority Data

Jun. 23, 2015  (KR) .................. 10-2015-0089090

(51) Int. Cl.
*C12N 5/0775*  (2010.01)
*G01N 33/50*  (2006.01)

(52) U.S. Cl.
CPC ......... *C12N 5/0662* (2013.01); *C12N 5/0667* (2013.01); *G01N 33/50* (2013.01); *G01N 33/5008* (2013.01); *G01N 33/5073* (2013.01); *C12N 2320/10* (2013.01); *C12N 2503/02* (2013.01); *C12N 2506/13* (2013.01); *C12N 2513/00* (2013.01); *C12N 2533/30* (2013.01)

(58) Field of Classification Search
CPC ............... C12N 5/0662; C12N 5/0667; C12N 2533/30; C12N 2320/10; C12N 2506/13; C12N 2513/00; C12N 2503/02; G01N 33/50; G01N 33/5073; G01N 33/5008
See application file for complete search history.

(56) References Cited

U.S. PATENT DOCUMENTS

2012/0134965 A1  5/2012  Kim et al.

FOREIGN PATENT DOCUMENTS

| KR | 1020100106905 A | 10/2010 |
|---|---|---|
| WO | 2014066649 A1 | 5/2014 |

OTHER PUBLICATIONS

Fennema et al. Spheroid culture as a tool for creating 3D complex tissues. Trends in Biotechnology Feb. 2013, vol. 31, No. 2. p. 108-115 (Year: 2013).*
Talele et al. Expression of a-Smooth Muscle Actin Determines the Fate of Mesenchymal Stromal Cells. Stem Cell Reports. vol. 4, p. 1016-1030. Jun. 9, 2015 (Year: 2015).*
Bunnell et al. Chapter 12: Differentiation of Adipose Stem Cells. Adipose Tissue Protocols. 2nd Ed. p. 155-171 (Year: 2008).*
Awad et al. Chondrogenic differentiation of adipose-derived adult stem cells in agarose, alginate, and gelatin scaffolds. Biomaterials 25 (2004) 3211-3222 (Year: 2004).*
Cheng et al., "The influence of spheroid formation of human adipose-derived stem cells on chitosan films on sternness and differentiation capabilities," Biomaterials, Nov. 20, 2011, pp. 1748-1758, vol. 33, No. 6, Elsevier Ltd.
Eleni Papakonstantinou et al., "Hypoxia modulates the effects of transforming growth factor-b isoforms on matrix-formation by primary human lung fibroblasts", Cytokine, 2003, pp. 25-35, vol. 24, Elsevier Ltd.
International Search Report dated Aug. 8, 2016 for PCT/KR2016/005501, citing the above references.
Kinoshita et al.,"Therapeutic Potential of Adipose-Derived SSEA-3-Positive Muse Cells forTreating Diabetic Skin Ulcers," Stem Cells Translational Medicine, Feb. 1, 2015, pp. 146-155, vol. 4, No. 2, AlphaMed Press.
Korean Office Action for corresponding Korean Patent Application No. 10-2015-0089090 dated Dec. 23, 2016, citing the above reference(s).
Park et al., Therapeutic Effect of Human Adipose-Derived Stromal Cells Cluster in Rat Hind-Limb Ischemia. The Anatomical Record 297:2289-2298 (2014) (Year:2014).
Qihe Xu et al., "In Vitro Models of TGF-B-induced Fibrosis Suitable for High-throughput Screening of Antifibrotic Agents", American Journal of Physiology-Renal Physiology, May 9, 2007, pp. F631-F640, vol. 293, No. 2.
Saleh Heneidi et al., "Awakened by Cellular Stress: Isolation and Characterization of a Novel Population of Pluripotent Stem Cells Derived from Human Adipose Tissue," PLOS ONE, Jun. 5, 2013, pp. 1-14, vol. 8, No. 6.
Sebastien Sart et al., "Three-Dimensional Aggregates of Mesenchymal Stem Cells: Cellular Mechanisms, Biological Properties, and Applications", Tissue Engineering: Part B, 2014, pp. 365-380, vol. 20, No. 5.
Solange Moll et al., "Epithelial Cells as Active Player in Fibrosis: Findings from an In Vitro Model", PLOS One, Feb. 14, 2013, pp. 1-6, vol. 8, No. 2.
Thanavel Rajangam et al., "3D human adipose-derived stem cell clusters as a model for in vitro fibrosis", Tissue Engineering Part C, Jan. 2016, pp. 1-41.
The Extended European Search Report dated Oct. 24, 2018 for corresponding European Patent Application No. 16814592.8, citing the above references.
Christina L. Rettinger, et al., "In vitro characterization of scaffold-free three-dimensional mesenchymal stem cell aggregates", Cell and Tissue Research, 2014, vol. 358, pp. 395-405.

(Continued)

*Primary Examiner* — Taeyoon Kim
(74) *Attorney, Agent, or Firm* — Cantor Colburn LLP

(57) ABSTRACT

Provided are an in vitro fibrosis model, a method of preparing the in vitro model, and use of the in vitro model, the in vitro model including a cell cluster differentiated from mesenchymal cells, wherein the cell cluster exhibits pathological characteristics of fibrosis.

4 Claims, 12 Drawing Sheets

(56) References Cited

OTHER PUBLICATIONS

Office Action dated Mar. 3, 2020 of Japanese Patent Application No. 2017-567167, which corresponds to the above-identified application.
Office Action dated Jan. 2, 2020 of Chinese Patent Application No. 201680003618.0, which corresponds to the above-identified application.
Vincent Falanga, et al., Low Oxygen tension Stimulates Collagen Synthesis and COL1A1 Transcription Through the Action of TGF-beta1, Journal of Cellular Physiology, No. 191, p. 42-50(2002).
S. K. Kapur, et al., Human adipose stem cells maintain proliferative, synthetic and multi potential properties when suspension cultured as self-assembling spheroids, Biofabrication 4 (2012) 025004 (12pp).

\* cited by examiner

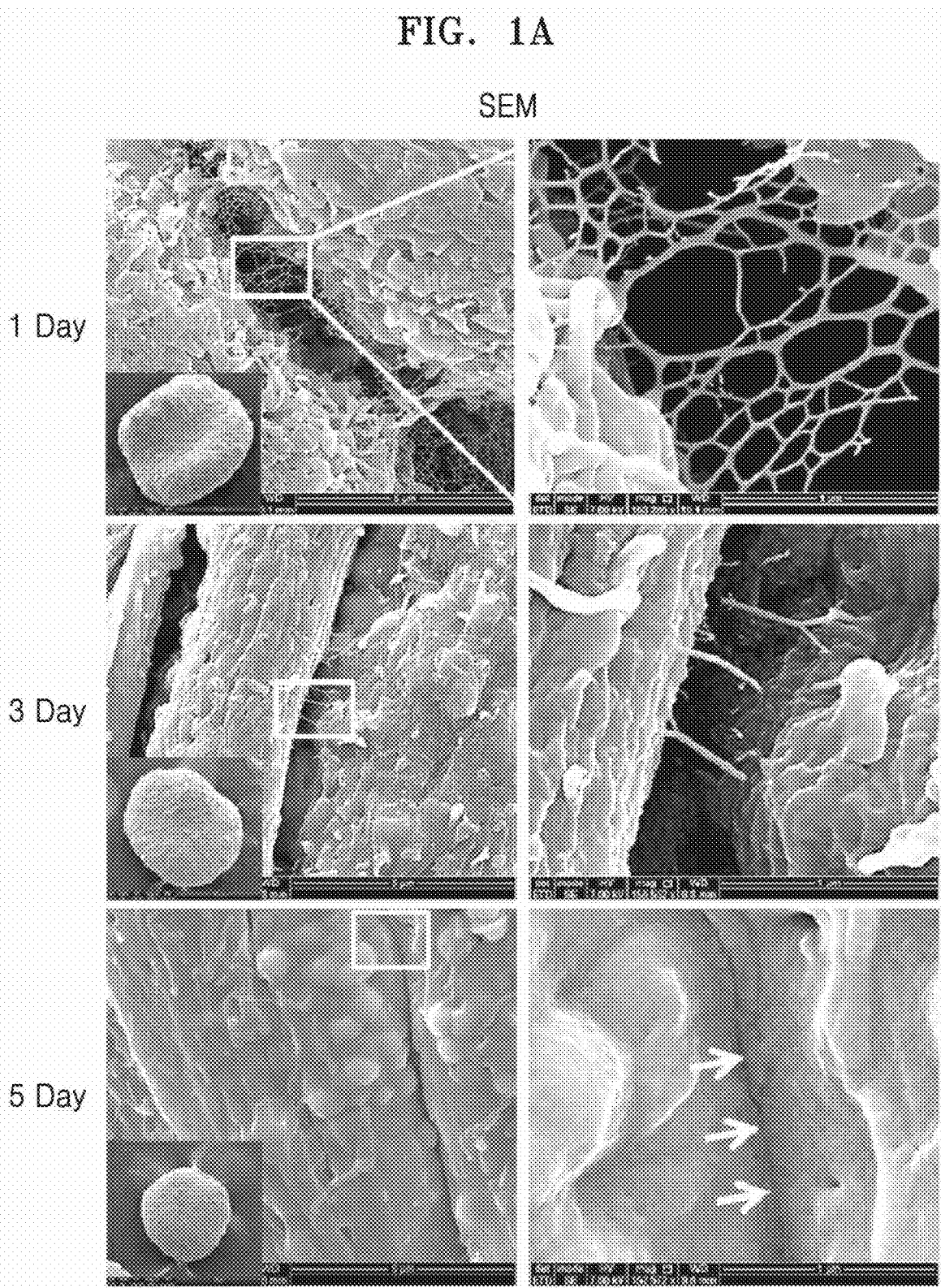

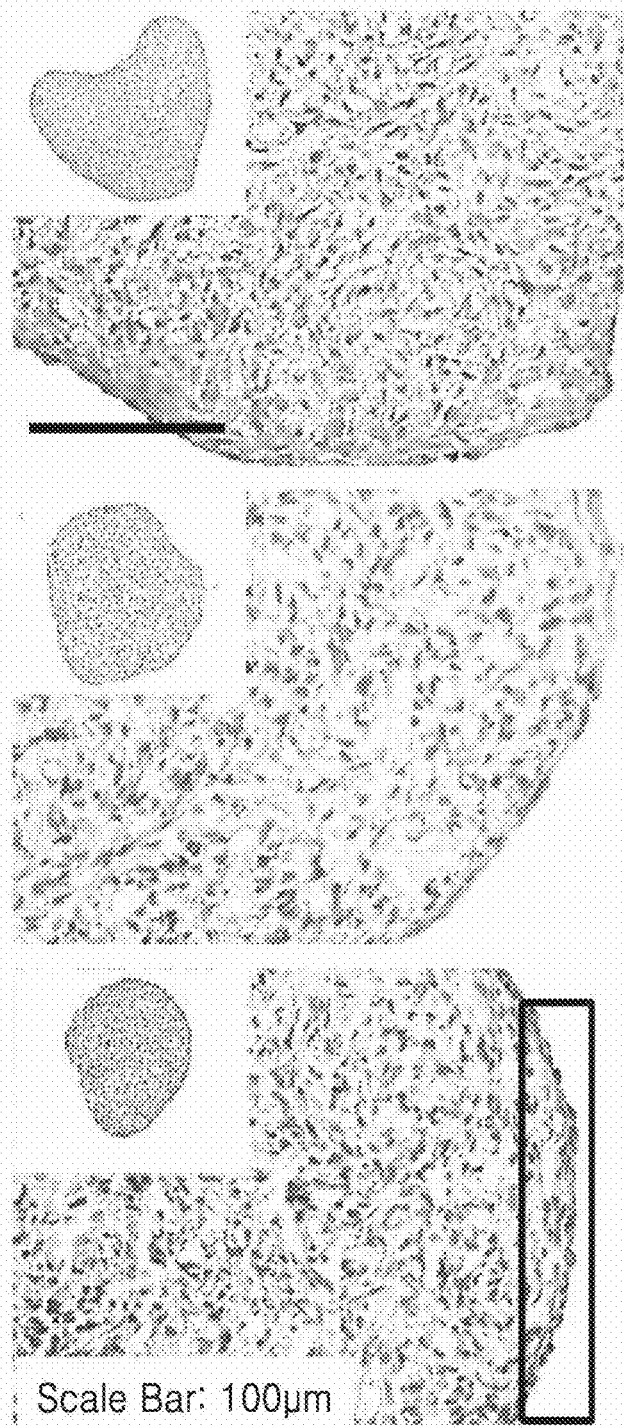

IN VITRO FIBROSIS MODEL, PREPARING METHOD THEREFOR, AND USE THEREOF

CROSS REFERENCE TO RELATED APPLICATIONS

This application is divisional of U.S. application Ser. No. 15/551,595, which is a National Stage application of PCT/KR2016/005501, filed May 25, 2016, which claims the benefit of Korean Patent Application No. 10-2015-0089090, filed Jun. 23, 2015, each of which is incorporated by reference in their entirety herein.

TECHNICAL FIELD

The present invention relates to an in vitro fibrosis model, a method of preparing the in vitro model, and use of the in vitro model.

BACKGROUND ART

More than 5 million people worldwide currently suffer from fibrosis, while each year 100,000 new patients are diagnosed with fibrosis and 40,000 patients die from fibrosis.

Fibrosis is characterized by the development of excessive connective tissue causing dysfunction and death of organs. Fibrosis generally affects various organs, such as the kidneys, liver, lungs, heart, skin, or bone marrow. Among these organs, renal fibrosis including renal tubulointerstitial fibrosis or focal segmental glomerulosclerosis is known to be difficult to treat and irreversible.

Meanwhile, administration of bleomycin into a mouse to prepare an experimental animal model of fibrosis or transformation of a mouse to prepare an animal model of pulmonary fibrosis has been known in the art. However, there is not yet a known model in in vitro systems for studying fibrous tissue and developing therapeutic agents. Therefore, in order to develop a therapeutic agent for fibrosis, the development of an in vitro fibrosis model that can mimic in vivo environments and exhibit pathological characteristics of fibrosis is required.

DETAILED DESCRIPTION OF THE INVENTION

Technical Problem

An aspect provides an in vitro fibrosis model including a cell cluster differentiated from mesenchymal cells, wherein the cell cluster exhibits pathological characteristics of fibrosis.

Another aspect provides a method of preparing an in vitro model, the method including: forming a cell cluster by adhering mesenchymal cells to a culture container comprising a hydrophobic surface and culturing the mesenchymal cells in the culture container; and establishing pathological characteristics of fibrosis in the cell cluster by performing additional culturing thereof for at least 12 hours.

Another aspect provides a method of screening a therapeutic agent for fibrosis, the method including: treating the in vitro fibrosis model with a test substance; and selecting, as a candidate substance for treatment of fibrosis, the test substance which exhibits improvement or treatment of pathological characteristics of fibrosis in the cell cluster or cells thereof in the in vitro fibrosis model, as compared with an untreated control group.

Technical Solution

An aspect provides an in vitro fibrosis model including a cell cluster differentiated from mesenchymal cells, wherein the cell cluster exhibits pathological characteristics of fibrosis.

The term "mesenchymal cells" used herein refers to pluripotent stem cells that can self-proliferate and differentiate into various lineages, and for example, refers to undifferentiated mesodermal cells that can differentiate into loose tissue between the mesoderm and the endoderm, connective tissue, dermis, subcutaneous tissue, bone, cartilage, bone marrow, skeletal muscle, smooth muscle, myocardium, blood cells, lymph nodes, lymphatic vessels, blood vessels, spleen, stomach, or the like. The mesenchymal cells may be separated from a subject, for example, a mammal including a human or the like, and may include adipose stem cells, mesenchymal stem cells, mesenchymal stromal cells, bone marrow stem cells, or fibroblasts. The term "separated" used herein in connection with the mesenchymal cells may refer to cells in an environment different from an environment within which cells are naturally produced. For example, considering that cells are naturally produced in multicellular organs and cells removed from the multicellular organs, cells are to be referred to as "separated" cells.

The term "cell cluster" or "three-dimensional (3D) cell cluster" (used interchangeably with the term 'cellular tissue') used herein refers to a state in which two or more cells are aggregated, and may be in the form of a tissue or in the form of single cells. Each cell cluster may be present in the tissue itself or in a part thereof, or may be present as a cluster of single cells. The cell cluster may include cell-like organization of cells differentiated from mesenchymal cells. In addition, the term "three-dimensional (3D)" refers to a structure having a model with three geometric parameters (for example, depth, width, and height, or X-, Y-, and Z-axes) rather than two dimensional parameters. In this regard, the cell cluster differentiated from the mesenchymal cells according to an embodiment may be cultured in a 3D manner. That is, the cell cluster may refer to a cell cluster consisting of cells that are adhered to a culture container, cultured in a floating state, and three-dimensionally formed into spheres, sheets, or similar three-dimensional forms (for example, a similar organizational body) upon the proliferation of the cells. Here, the cell cluster may have a diameter of 300 μm or more, and for example, may have a diameter in a range of about 300 μm to about 2,000 μm, about 400 μm to about 1,500 μm, or about 400 μm to about 1,000 μm. In addition, the cell cluster may include vascular cells differentiated from the mesenchymal cells, and for example, may include vascular cells at a density in a range of about $2\times10^4$ cells/cm$^2$ to about $1\times10^5$ cells/cm$^2$.

The differentiation of the mesenchymal cells into the cell cluster may be performed by adhering mesenchymal cells to a culture container including a hydrophobic surface and culturing the mesenchymal cells in the culture container. In detail, when the mesenchymal cells are cultured through adhesion to a culture container including a hydrophobic surface, the adhered mesenchymal cells may be separated from the culture container as a density of the mesenchymal cells increases, to thereby form a cell cluster. In addition, after the mesenchymal cells are differentiated into the cell cluster, the culturing of the mesenchymal cells may be further performed for at least 12 hours, at least 1 day, for example, for 12 hours to 15 days, for 1 to 15 days, for 3 to 10 days, for 3 to 7 days, or for 5 to 7 days. A detailed description of a method of forming the cell cluster through culturing will be described below.

The pathological characteristics of fibrosis may include symptoms that are specific or nonspecific to fibrosis, histomorphologic characteristics that are specific or nonspecific to fibrosis, molecular biological characteristics, or pathological characteristics. For example, the pathological characteristics of fibrosis may include at least one selected from the group consisting of: formation of excessive connective tissue as compared with connective tissue in fibrosis-free cells or tissue; deposition of collagen; increased expression, secretion, or synthesis of a fibrosis-related molecule; and increased cell death, or a combination thereof. The fibrosis-related molecule may include a marker gene or protein that is specific or nonspecific to fibrosis, and for example, may include at least one selected from the group consisting of transforming growth factor-beta (TGF-beta), Smad, laminins, and smooth muscle actin (SMA). The TGF-beta may include TGF-β1, 2, or 3, and the Smad may include any of Smads 1 to 8, R-Smad, Co-Smad, and I-Smad. The SMA, which is a marker of a myofibroblast, may cause the deposition of collagen in fibrosis. Therefore, the cell cluster according to an embodiment or cells constituting the cell cluster may exhibit such pathological characteristics of fibrosis as described above.

The term "fibrosis" used herein refers to formation of excessive fibrous connective tissue in an organ or tissue. The fibrosis may include at least one selected from the group consisting of idiopathic pulmonary fibrosis (IPF), pulmonary fibrosis, interstitial lung disease, nonspecific interstitial pneumonia (NSIP), usual interstitial pneumonia (UIP), endomyocardial fibrosis, mediastinal fibrosis, bone marrow fibrosis, retroperitoneal fibrosis, progressive massive fibrosis, nephrogenic systemic fibrosis, Crohn's disease, chronic myocardial infarction, scleroderma/systemic sclerosis, neurofibromatosis, Hermansky-Pudlak syndrome, diabetic kidney disease, renal fibrosis, hypertrophic cardiomyopathy (HCM), hypertension-related nephropathy, renal tubulointerstitial fibrosis, focal segmental glomerulosclerosis (FSGS), radiation-induced fibrosis, fibroids, alcoholic liver disease, liver steatosis, liver fibrosis, liver cirrhosis, Hepatitis C Virus (HCV) infection, chronic rejection of a transplanted organ, fibrotic skin disease, keloidal scar, Dupuytren's contracture, Ehlers-Danlos syndrome, epidermolysis bullosa dystrophica, oral submucous fibrosis, and fiber proliferative disorder.

Since the cell cluster differentiated from the mesenchymal cells according to an embodiment is cultured three-dimensionally, the cell cluster can mimic in vivo environments and have a phenotype of fibrosis, i.e., pathological characteristics of fibrosis, to be utilized in the in vitro fibrosis model. The term "fibrosis model" used herein refers to a model configured to schematize a structure or form of an organ, tissue, or cell having fibrosis, or also refers to a fibrosis model configured to elucidate the interaction between organs, tissues, or cells having fibrosis, or the relationship of structure or morphology of organs, tissues, or cells having fibrosis. Therefore, the fibrosis model may have a phenotype specific or nonspecific to fibrosis, or show expression of a marker gene or protein that is specific or nonspecific to fibrosis.

Another aspect provides a method of preparing the in vitro fibrosis model, the method including: forming a cell cluster by adhering mesenchymal cells to a culture container comprising a hydrophobic surface and culturing the mesenchymal cells in the culture container; and; and establishing pathological characteristics of fibrosis in the cell cluster by performing additional culturing thereof for at least 12 hours.

The mesenchymal cells, the cell cluster, and the fibrosis are the same as described above.

The mesenchymal cells may be adhered to the culture container by cell-substrate interactions with the hydrophobic surface of the culture container. The mesenchymal cells (for example, adipose stem cells) may be, for example, separated from human adipose tissue. The human adipose tissue may include mature adipocytes and connective tissue surrounding the mature adipocytes, and may be easily obtained from a patient or others having a phenotype matching that of a patient. Here, regardless of the position in the body, all the adipose tissues obtained by all the methods used for collecting fat may be used, and examples of the adipose tissues include subcutaneous fat tissue, bone marrow fat tissue, mesenteric adipose tissue, gastrointestinal adipose tissue, and retroperitoneal adipose tissue. The adipose stem cells may be separated from the above-described human adipose tissue according to a method known in the art. For example, as disclosed in WO2000/53795 and WO2005/04273, the adipose stem cells may be obtained from the adipose tissue by liposuction, sedimentation, enzyme treatment using collagenase or the like, removal of floating cells such as red blood cells by centrifugation, and the like. In addition, the mesenchymal cells, for example, mesenchymal stem cells, mesenchymal stromal cells, bone marrow stem cells, or fibroblasts, may be separated from various tissues by a method known in the art.

The separated mesenchymal cells exhibit an excellent proliferation rate up to a passage number of 16 even after several passages. Thus, for subsequent formation of a three-dimensional cell cluster, the pluripotent mesenchymal cells separated from the human tissue use cells cultured through 1 passage or cells cultured through 10 or more passages at confluency of 60%.

When the mesenchymal cells prepared as described above are cultured by inoculation into the culture container including a hydrophobic surface, due to the hydrophobic surface of the culture container, cell-substrate interactions occur between the mesenchymal cells and the culture container. In this regard, due to physical adsorption, the mesenchymal cells proliferate while being adhered to the surface of the culture container. Afterwards, the forming of the cell cluster may refer to formation of the cell cluster such that the adhered mesenchymal cells may be separated from the culture container as a density of the mesenchymal cells increases.

A cell culture container that is surface-treated with a polymer that imparts hydrophobicity to a conventional cell culture container, or a cell culture formed of such a polymer, may be suitable for use as the culture container including the hydrophobic surface in the present inventive concept. Such a hydrophobic polymer may be one selected from polystyrene, polymethyl methacrylate (PMMA), polyethylene terephthalate (PET), polyvinyl chloride (PVC), polyethylene (PE), polypropylene (PP), poly(tetrafluoroethylene) (PTFE), and an aliphatic polyester-based polymer selected from poly(L-lactic acid) (PLLA), poly(D,L-lactic acid) (PDLLA), a poly(glycolic acid) (PGA), poly(caprolactone) (PCL), poly (hydroxyalkanoate), polydioxanone (PDS), and poly(trimethylene carbonate), or may be a copolymer of units above, such as poly(lactic acid-co-glycollic acid) (PLGA), poly(L-lactic acid-co-caprolactone) (PLCL), poly(glycolic acid-co-caprolactone) (PGCL), or a derivative thereof. In addition, the hydrophobic surface of the culture container may be a silanized surface, a carbon nanotube (CNT) surface, a hydrocarbon-coated surface, or a metallic (for example, stainless steel, titanium, gold, platinum, or the like) surface.

In addition, in one or more embodiments of the present invention, in order to more effectively adhere the mesenchymal cells to the culture container than by physical adsorption through the interaction between the mesenchymal cells and the hydrophobic surface of the culture container, the mesenchymal cells may be adhered to the culture container through an interaction with a growth factor having adhesiveness to the mesenchymal cells. For example, after such a growth factor is immobilized on the surface of the culture container, a biochemical interaction between the immobilized growth factor and the mesenchymal cells may be utilized.

The growth factor may have be any substance having adhesiveness to the mesenchymal cells, and examples thereof are vascular endothelial growth factor (VEGF), fibroblast growth factor (FGF), epidermal growth factor (EGF), platelet-derived endothelial growth factor (PDGF), hepatocyte growth factor (HGF), insulin-like growth factor (IGF), or heparin-binding domain (HBD). The growth factor may be immobilized on the surface of the culture container at a concentration in a range of about 5 µg/ml to about 100 µg/ml.

The immobilization of the growth factor on the surface of the culture container may be achieved by a method known in the art, the method being used to immobilize a polypeptide on a solid substrate surface, and for example, the immobilization may be performed by physical adsorption or covalent bonding by a non-selective chemical reaction. As the immobilization method, a method of immobilizing a protein using biotin-streptavidin/avidin bonds by binding biotin to a protein and then applying the protein to a solid surface treated with streptavidin or avidin; a method of immobilizing a protein by integrating an active group (a chemical functional group for immobilizing a protein by a chemical bond) with a substrate using plasma; a method of immobilizing a protein by physical adsorption to a porous sol-gel thin film after forming the porous sol-gel thin film having a sufficiently increased specific area on a solid substrate surface according to a sol-gel method; a method of immobilizing anticoagulant protein on a poly(tetrafluoroethylene) (PTFE) surface by plasma reaction; a method of immobilizing a protein by binding with an enzyme, in which two or more cationic amino residues are fused to two enzymes sequentially; a method of immobilizing a protein on a hydrophobic polymer layer bonded to a solid support using a substrate; a method of immobilizing a protein on a plastic surface using a buffering component; or a method of immobilizing a protein by contacting a hydrophobic solid surface with an alcohol solution, is known in the art.

In one embodiment, a polypeptide linker that can be subjected to recombinant mass expression and easy purification may be used to perform immobilization in the form of a peptide linker-growth factor recombinant protein in which an amino terminus of the growth factor is fused to a carboxyl terminus of the polypeptide linker.

A substance capable of being adhered to the culture container including the hydrophobic surface through a hydrophobic domain present at an amino terminus of a growth factor to which a carboxyl terminus of the polypeptide linker is bonded, or a substance that can be subjected to recombinant mass expression and easy purification without being adversely affected, may be suitable for use as the polypeptide linker in the present invention. Examples of the polypeptide linker are a maltose-binding protein (MBP), a hydrophobin, or a hydrophobic cell penetrating peptide (CPP).

As such, when the mesenchymal cells are cultured by physical adhesion through cell-substrate interactions with the hydrophobic surface of the culture container, or when the mesenchymal cells are cultured in the state of being bound to a growth factor through a biochemical interaction with the growth factor immobilized on the surface of the culture container, the mesenchymal cells can proliferate while being adhered to the surface of the culture container at the beginning. The mesenchymal cells may be seeded at a concentration in a range of about $1\times10^3$ cells/cm$^2$ to about $1\times10^7$ cells/cm$^2$. In addition, a temperature for the culturing of the mesenchymal cells may be in a range of about 35° C. to about 38.5° C., and a culture period required for the formation of the cell cluster may be 4 hours to 2 days, or for example, 1 day. As a suitable medium for the culturing of the mesenchymal cells, a serum-containing or serum-free medium conventionally used for culturing and/or differentiation of the mesenchymal cells may be used without limitation, and examples thereof are a Dulbeco's modified eagle medium (DMEM), Ham's F12, or a medium in which serum is added to a mixture of the above substances.

Then, when the mesenchymal cells proliferate in a state in which they are adhered to the surface of the culture container, and the cell-cell interactions become stronger than cell-substrate interactions at high cell densities, the mesenchymal cells become separated from the surface of the culture container and then proliferate while floating in the culture. The floating mesenchymal cells then aggregate together such that a floating three-dimensional cell cluster having a size detectable with the naked eye may be formed.

In one embodiment, considering the hydrophobic surface of the culture container, a non-tissue culture plate (NTCP) made of polystyrene is used as a culture container in which cell adhesion to such a hydrophobic surface is relatively weak, and the mesenchymal cells are inoculated thereto to induce formation of a three-dimensional cell cluster. The mesenchymal cells inoculated to the polystyrene NTCP initially undergo induction of weak cell adhesion to a surface of the polystyrene NTCP by cell-substrate interactions, and then proliferate in a two-dimensional single layer in a state in which they are adhered to the surface of the polystyrene NTCP. However, as the cell density increases as the culture time elapses, the cell-cell interactions become stronger than the cell-substrate interactions, thereby separating the mesenchymal cells cultured in the two-dimensional single layer from the surface of the polystyrene NTCP. Here, the mesenchymal cells can initially be cultured in a state in which they are adhered to the surface of the culture container, whereas, in the case where the mesenchymal cells are initially cultured in a floating state without undergoing cell adhesion, a three-dimensional cell cluster formed therefrom may have a small size and include cells that mostly undergo cell apoptosis. When the mesenchymal cells separated from the culture container are further cultured in a floating state in a culture fluid, the mesenchymal cells may aggregate together through cell-cell interactions to thereby form a three-dimensional cell cluster. In the three-dimensional cell cluster formed therefrom, the mesenchymal cells are initially weakly bound, but as the culture time elapses, the cell-cell interactions enhance adhesion between the mesenchymal cells constituting the cell cluster to thereby form a compact three-dimensional cell cluster.

In addition, when the formed cell cluster is further cultured for at least 12 hours, the cell cluster or the cells of the cell cluster may exhibit the pathological characteristics of fibrosis. Here, the additional culture time may be at least 12 hours or at least 1 day, and for example, may be from 12 hours to 15 days, 1 to 15 days, 3 to 10 days, 3 to 7 days, or 5 to 7 days. The pathological characteristics of fibrosis are the same as described above.

The three-dimensional cell cluster may be differentiated into vascular endothelial cells by proliferation in the form of the formed three-dimensional cell cluster. When the mesenchymal cells are cultured in the form of the three-dimensional cell cluster, oxygen permeation into the cell cluster decreases upon the formation of the cell cluster, and accordingly, a hypoxic state may thereby be formed. Such a hypoxic state formed in the cell cluster induces production of various angiogenic factors that affect the differentiation into vascular endothelial cells, resulting in differentiation into vascular endothelial cells.

The three-dimensional cell cluster formed by culturing the mesenchymal cells through adhesion to the surface of the culture container has a size detectable with the naked eye, and for example, has a diameter in a range of about 300 μm to about 2,000 μm. In this regard, the formed three-dimensional cell cluster may be easily recovered by a method such as filtration or centrifugation. The recovered three-dimensional cell cluster may be subjected to enzymatic treatment with collagenase, trypsin, or dispase, mechanical treatment with pressure, or combinational treatment, to thereby break up the cluster form into the form of single cells, or the three-dimensional cell cluster form itself may be used.

Another aspect provides a method of screening a therapeutic agent for fibrosis, the method including: treating the in vitro fibrosis model with a test substance; and selecting, as a candidate substance for treatment of fibrosis, the test substance exhibiting improvement or treatment of pathological characteristics of fibrosis in the cell cluster or cells thereof in the in vitro fibrosis model, as compared with an untreated control group.

The mesenchymal cells, the cell cluster, and the fibrosis are the same as described above.

In the method of screening the therapeutic agent for fibrosis, the test substance may include one selected from the group consisting of a low-molecular weight compound, an antibody, an antisense nucleotide, a short interfering RNA, a short hairpin RNA, a nucleic acid, a protein, a peptide, and other extracts and natural substances.

In addition, in the method of screening the therapeutic agent for fibrosis, the pathological characteristics of fibrosis include symptoms that are specific or nonspecific to fibrosis, histomorphologic characteristics that are specific or nonspecific to fibrosis, molecular biological characteristics, or pathological characteristics. For example, the pathological characteristics of fibrosis may include at least one selected from the group consisting of: formation of excessive connective tissue as compared with connective tissue in a fibrosis-free cell or tissue; deposition of collagen; increased expression, secretion, or synthesis of a fibrosis-related molecule; and increased cell death, or a combination thereof. The fibrosis-related molecule may include a marker gene or protein that is specific or nonspecific to fibrosis, and for example, may include at least one selected from the group consisting of TGF, Smad, laminins, and SMA. The TGF-beta may include TGF-$\beta$1, 2, or 3, and the Smad may include any of Smads 1 to 8, R-Smad, Co-Smad, and I-Smad. The SMA which is a marker of a myofibroblast may cause the deposition of collagen in fibrosis. Therefore, for example, regarding the selecting of the test substance for treatment of fibrosis, in a case where, as compared to an untreated control group, connective tissue is formed in the cell cluster or in cells constituting the cell cluster, collagen is deposited, a thickness of collagen fibers decreases, or viability of cells increases in a test substance-treated group, the test substance may be selected as the candidate substance for treatment. The phenotype of fibrosis, i.e., formation of excessive connective tissue, deposition of collagen, or measurement of a thickness of collagen fibers, may be identified according to the methods known to one of ordinary skill in the art, such as a Haematoxylin and Eosin (H&E) staining method, a Masson-trichrome (MT) staining method, an immunofluorescence method, or an immunohistochemical staining method. In addition, the viability or apoptosis of cells may be identified according to an LDH assay or a live/dead assay. In addition, in cases where the test substance increases or decreases expression of a fibrosis-related molecule, i.e., a marker gene or protein that is specific or nonspecific to fibrosis, the test substance may be selected as the candidate substance for treatment of fibrosis. For example, in cases where the test substance decreases expression of TGF-beta, Smad, laminin, or SMA, the test substance may be selected as the candidate substance for treatment of fibrosis. Such expression may be measured by one selected from the group consisting of reverse transcriptase polymerase chain reaction (RT-PCR), enzyme linked immunosorbent assay (ELISA), immunohistochemistry, western blotting, and fluorescence-activated cell sorting (FACS).

Advantageous Effects of the Invention

According to embodiments regarding the in vitro fibrosis model and the method of preparing the same, the in vitro fibrosis model which is formed as a three-dimensional cell cluster is able to mimic in vivo environments and exhibit the fibrosis phenotype, i.e., pathological characteristics of fibrosis, and thus the disclosure of the present invention may be effectively used for research on fibrosis or a screening method for a therapeutic agent.

DESCRIPTION OF THE DRAWINGS

FIG. 1A shows scanning electron microscope (SEM) images of a three-dimensional cell cluster according to an embodiment;

FIG. 1B shows Haematoxylin and Eosin (H&E) staining results obtained from a three-dimensional cell cluster according to an embodiment;

MODE OF THE INVENTION

Figure 2:
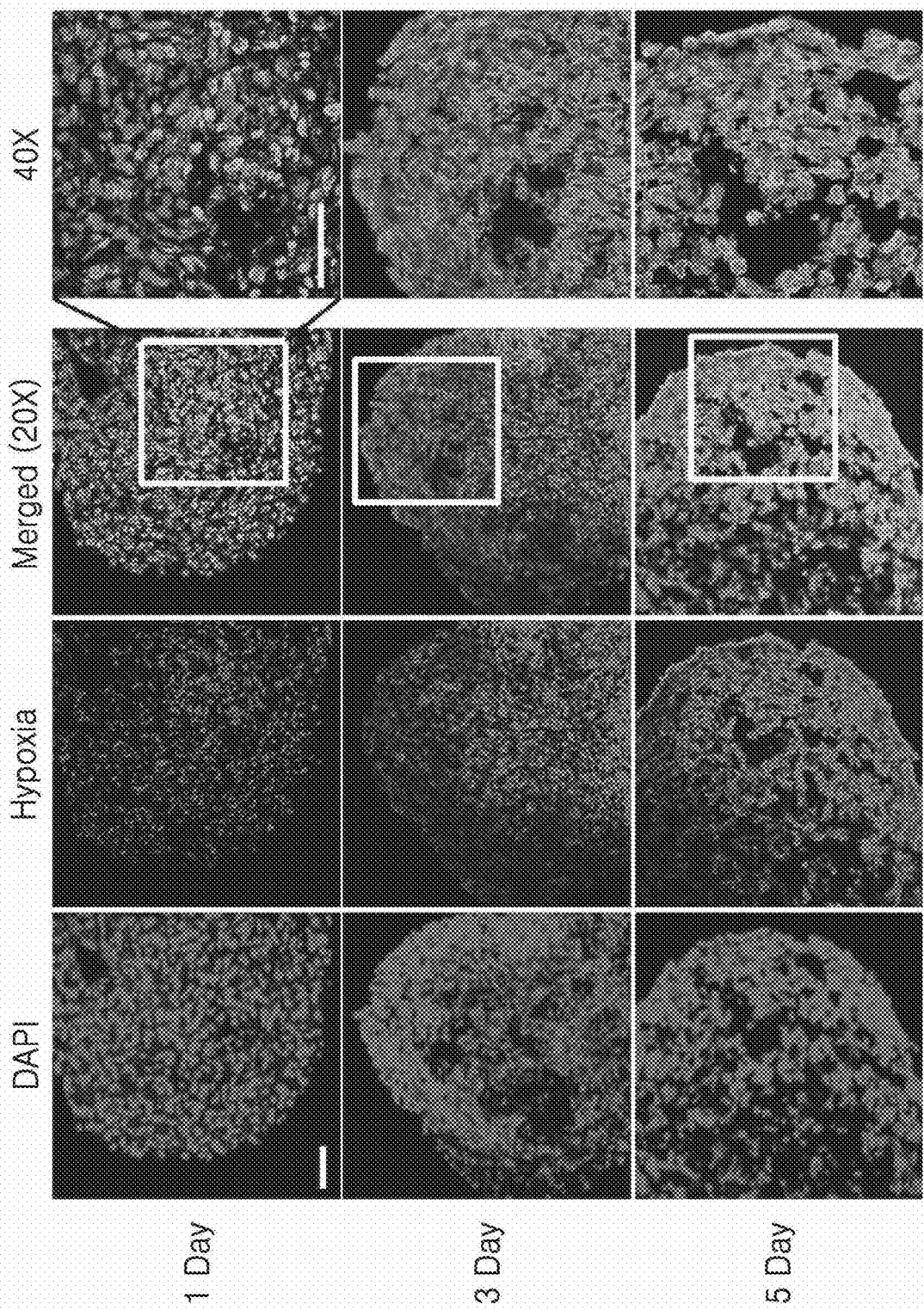
FIG. 2 is a diagram showing immunofluorescence staining results confirming a hypoxic state of a three-dimensional cell cluster according to an embodiment.

Hereinafter, the present invention is described in detail with reference to Examples. However, Examples shown and described herein are illustrative examples of the present invention and are not intended to otherwise limit the scope of the inventive concept in any way.

Examples: Preparation of In Vitro Fibrosis Model and Characterization of Fibrosis Modeling (1) Preparation of In Vitro Fibrosis Model (1.1) Separation of Human Adipose Stem Cells (hASCs)

Subcutaneous adipose tissue of normal individuals was obtained from the Department of Plastic Surgery, the Catholic University of Korea. Then, the adipose tissue was washed three times with PBS containing 1% penicillin/streptomycin (PS) to remove contaminated blood therefrom, and was cut with surgical scissors. The resulting adipose tissue was soaked in a tissue lysate containing 1% BSA (w/v), 0.3% collagenase type I, and 1% PS, and then, the mixed tissue lysate was stirred by orbital shaking for 1 hour at a temperature of 37° C. Afterwards, the supernatant was removed, and the cell suspension was filtered through a 250 μm Nitex filter (Sefar America Inc.) to remove tissue debris. Then, centrifugation was performed thereon at a speed of 1,000 rpm for 5 minutes. Cells collected by centrifugation were re-suspended in DMEM/F-12 containing 10% BSA. The isolated primary cells were plated in a tissue culture flask for 24 hours in a humidified atmosphere with 5% $CO_2$ and 95% air. Then, non-adherent cells were removed by replacement with a fresh medium having the same volume. The morphology of adherent hASCs was observed via a phase contrast microscope, and hASCs of 5 passages were used for all experiments.

(1.2) Preparation of 3D Cell Cluster Derived from Adipose Stem Cells

To prepare a 3D cell cluster derived from the hASCs, the hASCs were cultured in a treated 96-well non-tissue culture plate (NTCP) (NTCP made of polystyrene and having a hydrophobic surface, Falcon Company). The NTCP was a plated coated with a fused protein of maltose binding protein (MBP)-fibroblast growth factor (FGF), wherein the plate coated with the fused protein has been described in KR 10-1109125 that is incorporated herein by reference in its entirety. In detail, $1\times10^5$ cells/cm$^2$ of the hASCs were inoculated into each well of the well plate, and cultured in a DMEM/F-12 medium containing 10% FBS. Within 24 hours of the culture, 3D cell clusters of the hASCs were formed on each cell adhesion surface. For analysis of characteristics of a fibrosis model with respect to the formed 3D cell clusters, 3D cell clusters were collected on the 1$^{st}$ day (1 Day), 3$^{rd}$ day (3 Day), and 5$^{th}$ day (5 Day) of the culture. In addition, the 3D cell clusters were confirmed to have a diameter of about 500 μm or more. Hereinafter, the 3D cell cluster was represented by '3DCM'.

In addition, as a comparative example, the hASCs were cultured in a 2D manner. In detail, $1\times10^5$ cells/cm$^2$ of the hASCs were inoculated into each well of a treated 96-well tissue culture plate (TCP), and cultured in a DMEM/F-12 medium containing 10% FBS. In the same manner as in the 3D cell cluster, cells were collected on the 1$^{st}$ day (1 Day), 3$^{rd}$ day (3 Day), and 5$^{th}$ day (5 Day) of the culture for analysis of characteristics of a fibrosis model. Hereinafter, the cells cultured in a 2D manner are represented by '2D'.

(2) Analysis of Fibrosis Modeling Characteristics of In Vitro Fibrosis Model (2.1) Analysis of Characteristics of 3D Cell Cluster Derived from Adipose Stem Cells To analyze the morphological characteristics of a 3D cell cluster derived from adipose stem cells, the 3D cell cluster was subjected to scanning electron microscopy and H&E staining. In addition, immunostaining was performed on the 3D cell cluster to confirm a hypoxic state in the 3D cell cluster.

In detail, for scanning electron microscopy, the collected 3D cell cluster was immobilized with 2.5% glutaraldehyde at a temperature of 4° C. for 2 hours, and then post-immobilized with 1% osmium tetroxide in deionized water. The immobilized 3D cell cluster was dehydrated two times with ethanol at a series of concentrations (50%, 70%, 80%, 90%, and 100%). Afterwards, the resulting 3D cell cluster was immersed in hexamethyldisilazane (HMDS) for 2 minutes, and vibration-dried for one day. To obtain an SEM image, the 3D cell cluster was attached to an adhesive carbon tape, and sputter-coating was performed with gold for 60 minutes at 10 mA. Images were then obtained at 15 kV, and the results are shown in FIG. 1A.

In addition, for H&E staining, the collected 3D cell cluster was immobilized with 4% PFA at room temperature for 30 minutes, dehydrated with ethanol at a series of concentrations (50%, 70%, 80%, 90%, and 100%), and then, placed in paraffin wax. A section having a thickness of 4 μm was prepared, and then stained with haematoxylin and eosin. The section was deparaffinized, hydrated with distilled water, and washed three times with PBS. Afterwards, the resulting section was immersed in haematoxylin (Harris; Sigma-Aldrich) for 10 seconds, washed in flowing water for 10 to 15 minutes, counter-stained with eosin for 15 seconds, and then, washed again for 10 to 15 minutes. Afterwards, the resulting section was placed on a slide to be observed with a light microscope, and the results are shown in FIG. 1B.

In addition, for hypoxic immunofluorescence analysis, the 3D cell cluster was incubated, before being collected at each culture time, in 10 mmol pimonidazole hydrochloride (Hypoxyprobe™-1 kit, Hypoxyprobe, USA) in 0.1 ml solution for 2 hours. Then, the incubated 3D cell cluster was collected, immobilized with 4% paraformaldehyde at a temperature of 4° C. for 30 minutes, and embedded in an optimal cutting temperature (OCT) compound (TISSUE-TEK® 4583; Sakura Finetek USA, Inc.). A frozen section having a thickness of 6 μm was washed with PBS, and to prevent nonspecific binding thereto, the 3D cell cluster was incubated in 4% BSA in PBS for 1 hour. Accordingly, pimonidazole was detected by primary mouse antibodies (hydroxy probe) and secondary goat anti-mouse Alexa 488 antibodies (Invitrogen). In addition, 4,5-diamino-2-phenylindole (DAPI) (Vector Laboratories) was used for nuclear staining. Here, a control group was subjected to experiments performed under the same conditions, except that no primary antibody was used, and was observed with a confocal microscope (Carl Zeiss). The results are shown in FIG. 2.

FIG. 1A shows SEM images and H&E staining results obtained from the 3D cell cluster according to an embodiment.

FIG. 2 is a diagram showing immunofluorescence staining results confirming a hypoxic state of the 3D cell cluster according to an embodiment.

As shown in FIG. 1, the outer surface the 3D cell cluster of the culture at Day 1 was densely stained by H&E, and thus, it was confirmed that the cells were connected by fibrous matrices. As the culture continued, the 3D cell cluster of the culture at Day 3 showed a decreased intercellular space between the cells, and the 3D cell cluster of the culture at Day 5 showed almost no gap between the cells (see arrows).

In addition, as shown in FIG. 2, it was confirmed that the DAPI-stained cells were uniformly distributed over the 3D cell cluster on Day 1 of the culture, and that more hypoxic probe-positive cells were present inside the 3D cell cluster. As the culture continued, the 3D cell cluster of Day 3 of the culture showed increased hypoxic probe-positive cells therein, and the 3D cell cluster of Day 5 of the culture also showed increased hypoxic probe-positive cells outside of the 3D cell cluster. Accordingly, it was confirmed that hypoxia was induced in the 3D cell cluster, and then, diffused to the outside of the 3D cell cluster. That is, by referring to FIG. 1, it was confirmed that the closure of the intercellular space on the outer surface of the 3D cell cluster led to the induction of hypoxia. In fibrosis, TGF-1 is an important relevant factor which is overexpressed in hypoxia. That is, as the distance between the cells narrowed, supply of oxygen to the cell cluster was restricted, and accordingly, TGF-1 was induced, thereby causing fibrosis. Therefore, based on the results above, it was confirmed that the pathological characteristics of fibrosis were modeled by the 3D cell cluster according to an embodiment.

(2.2) Analysis of Fibrosis-Related Factors in 3D Cell Cluster Derived from Adipose Stem Cells TGF-beta is a major molecule in fibrosis and is induced under hypoxic conditions. To confirm whether fibrosis-related factors have been expressed or not in the 3D cell cluster derived from adipose stem cells, ELISA was performed on fibrosis-related factors including TGF-beta.

In detail, to measure total contents of TGF-β1, a culture medium was prepared with normal cell concentration (NCC), 2D cells (2D), and 3D cell cluster (3DCM). To activate latent TGF-β1 in an immunoreactive form, the culture supernatant was incubated in 1N HCL and neutralized with 1.2 N NaOH/0.5 M HEPES. The assay was performed using the Quantikine ELISA human TGF-β1 kit (R&D System) according to the manufacturers instructions. Here, the absorbance was measured using a Multiskan (Thermo) at 560 nm, and the results are shown in FIG. 3.

In addition, to confirm the expression of the fibrosis-related factors in the 3D cell cluster, total RNAs were extracted from the collected 3D cell cluster by using a triazole reagent (Invitrogen, USA) according to the manufacturer's instructions. The extracted RNAs were dissolved in nuclease-free water, and then, the concentration of the resulting RNAs was quantified using a NanoDrop ND1000 spectrophotometer (Thermo Fisher Scientific). Here, synthesis of complementary DNA was performed by using Maxime RT PreMIX (iNtROn) according to the manufacturers instructions. All target primers were purchased from Bioneer. All polymerase chain reactions were performed using ABI Prism 7500 (Applied Biosystems), and gene expression levels were quantified using SYBR Premix Ex Taq (TaKaRa). Comparative gene expression levels were calculated using the comparative Ct method, and the results are shown in FIG. 4.

Figure 3:
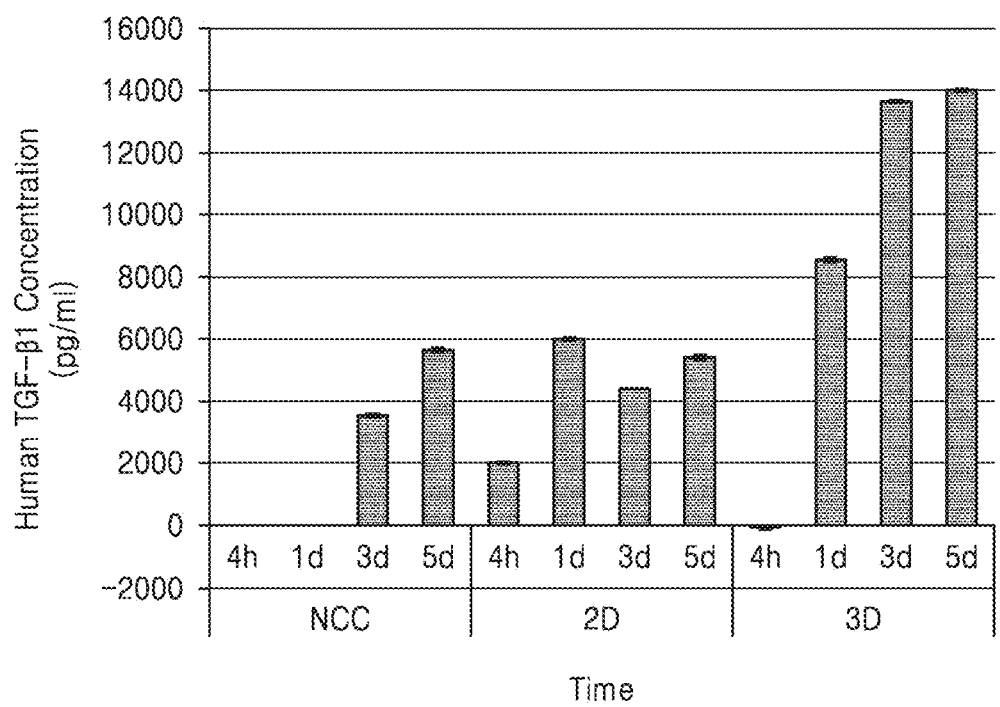
FIG. 3 is a graph showing expression of TGF-beta in a three-dimensional cell cluster according to an embodiment.

FIG. 3 is a graph showing the expression of TGF-beta in the 3D cell cluster according to an embodiment.

Figure 4:
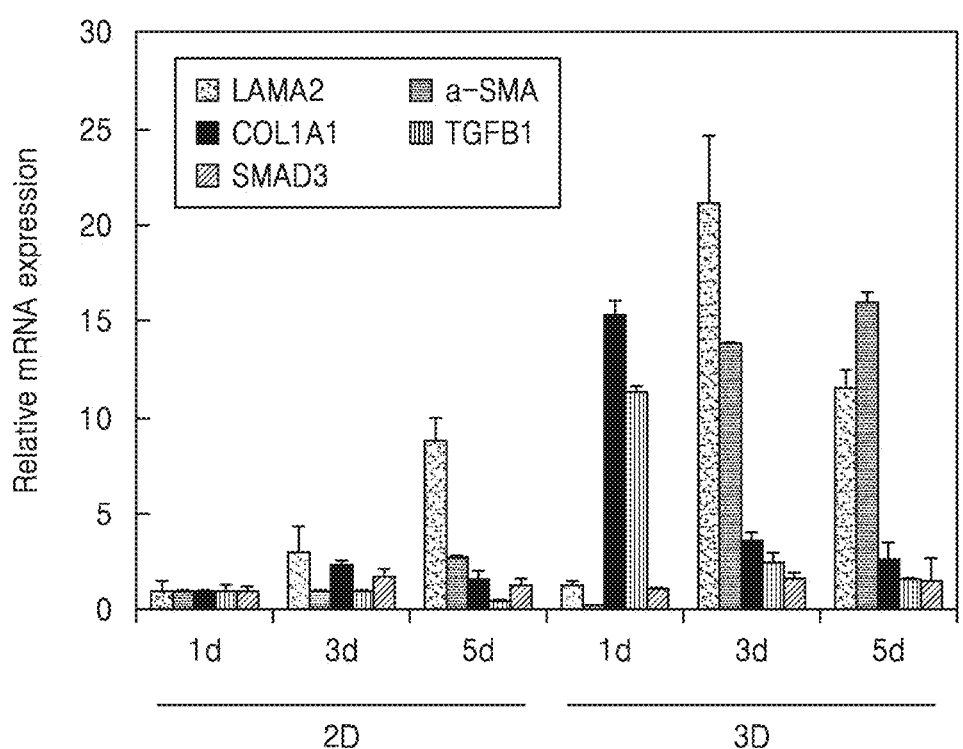
FIG. 4 is a graph showing expression of fibrosis-related factors in a three-dimensional cell cluster according to an embodiment.

FIG. 4 is a graph showing the expression of fibrosis-related factors in the 3D cell cluster according to an embodiment.

As shown in FIGS. 3 and 4, it was confirmed that the 3D cell cluster derived from adipose stem cells showed increased expression of the fibrosis-related factors including TGF-beta, laminin, smooth muscle actin (SMA), collagen type I, and SMAD3.

(2.3) Analysis of Collagen Deposition in 3D Cell Cluster Derived from Adipose Stem Cells To analyze collagen deposition in the 3D cell cluster derived from adipose stem cells, the 3D cell cluster was subjected to immunofluorescence staining, immunohistochemical staining, and hydroxyproline quantification, and observed with a transmission electron microscope.

Figure 5A:
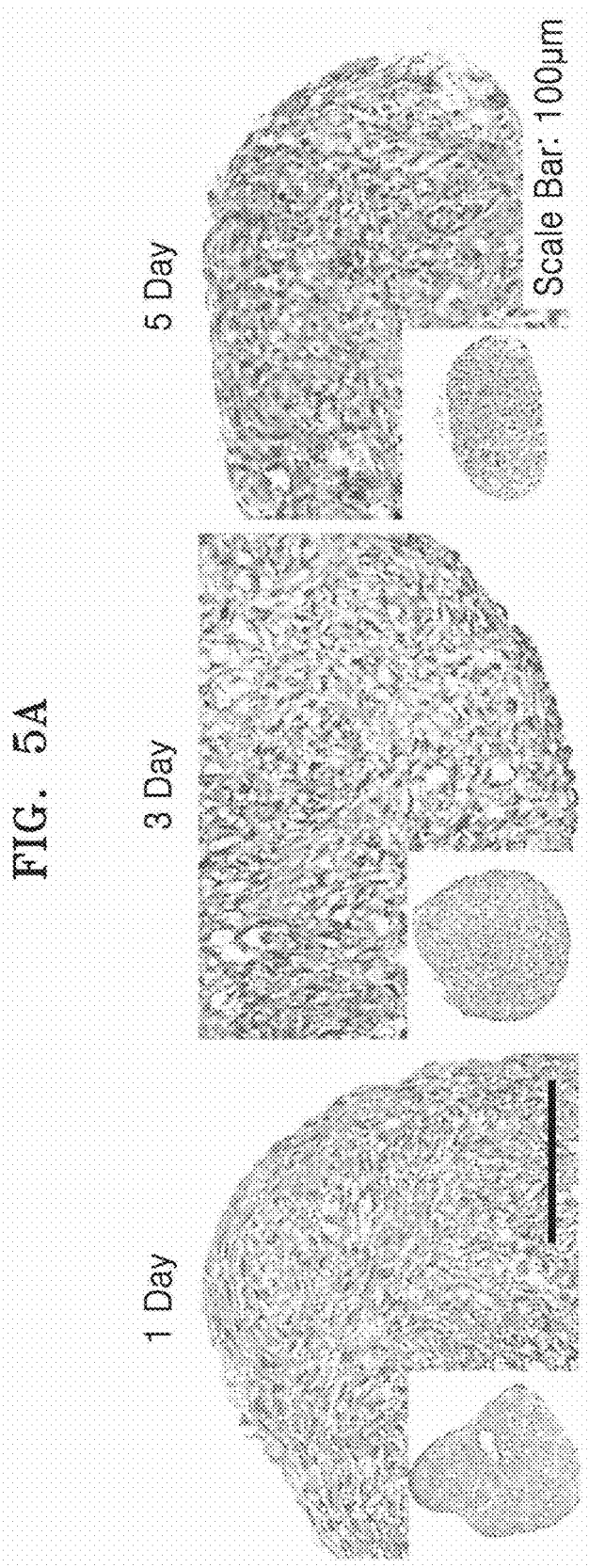
FIG. 5A is a diagram showing results for deposition of collagen in a three-dimensional cell cluster according to an embodiment, as identified by immunofluorescence staining and analysis of hydroxyproline contents.
Figure 5B:
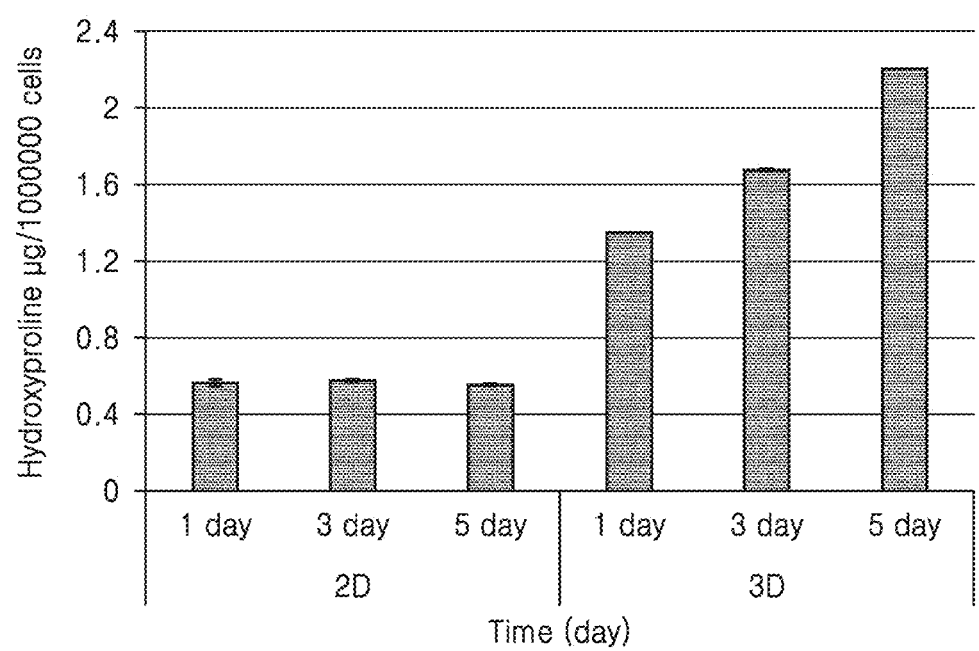
FIG. 5B is a graph showing results for deposition of collagen in a three-dimensional cell cluster according to an embodiment, as identified by immunofluorescence staining and analysis of hydroxyproline contents.

In detail, pretreatment was performed on the 3D cell cluster in the same manner as in H&E staining, and staining was performed thereon using Masson's trichrome (MT) staining. In the 3D cell cluster, the percentage of fibrosis was determined by counting the number of pixels of the stained collagen area in a digital image by using the ImageJ software (NIH), and the results are shown in FIG. 5A. In addition, for a hydroxyproline assay, 2D cells and 3D cell cluster were prepared by using RIPA buffer, and then, were hydrolyzed in 12N HCL at a temperature of 120° C. for 3 hours. Assays were performed using the hydroxyproline kit (Sigma-Aldrich) according to the manufacturer's instructions. Here, the absorbance was measured using a Multiskan (Thermo) at 560 nm, and the results are shown in FIG. 5B.

Figure 6:
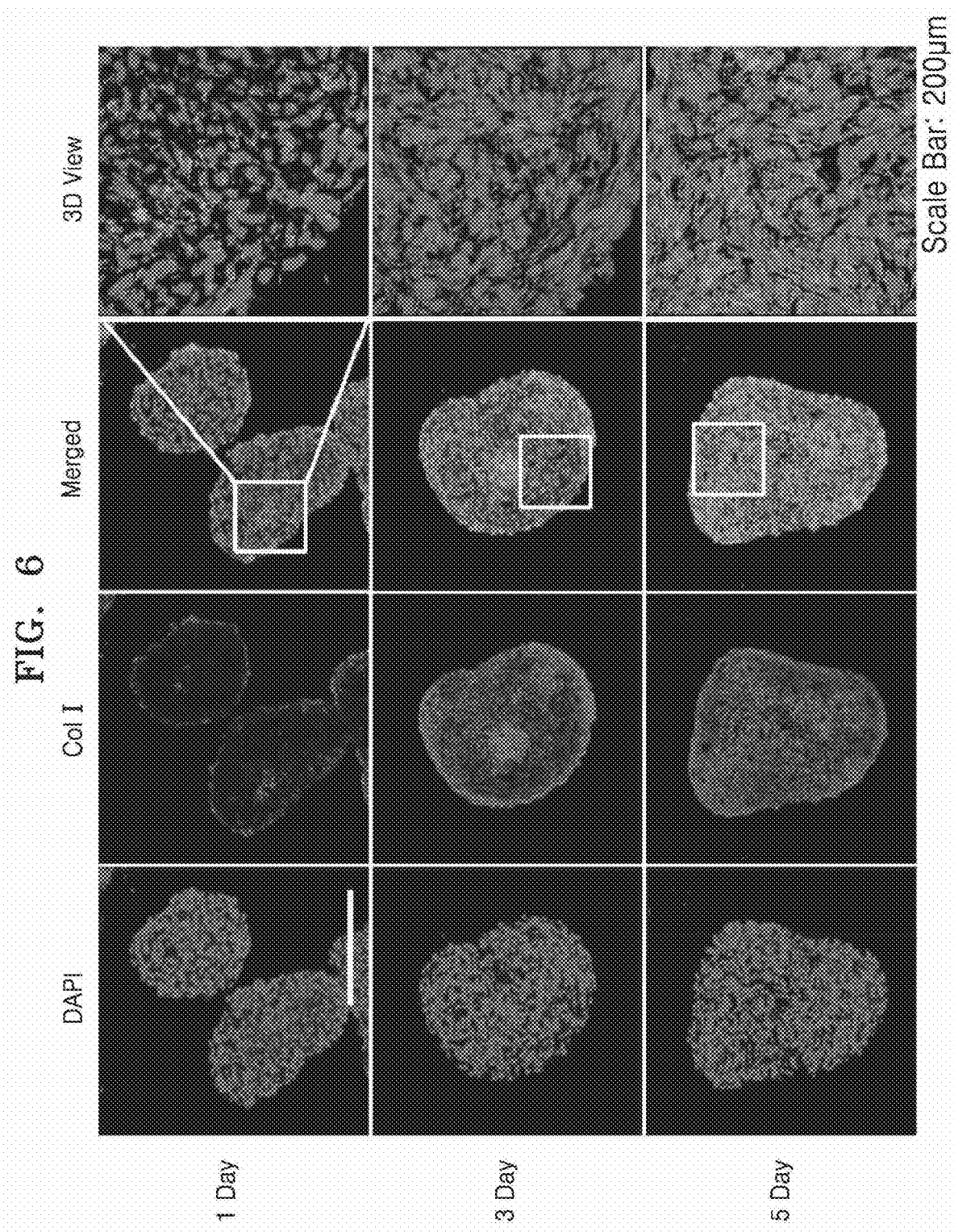
FIG. 6 is a diagram showing results for deposition of collagen type I in a three-dimensional cell cluster according to an embodiment, as identified by immunofluorescence staining.

In addition, for immunofluorescence (IF), a 3D cell cluster was immobilized in the same manner as in H&E staining above, embedded in an OCT compound (TISSUE-TEK® 4583; Sakura Finetek USA, Inc.), and then frozen at a temperature of −28° C. The resulting 3D cell cluster was cut to a thickness of 6 μm. To avoid nonspecific binding thereto, a section was incubated in 4% BSA at room temperature for 1 hour. Afterwards, the section was incubated overnight at a temperature of 4° C. with primary antibodies (Rabit, Abicam) specific for collagen type I. Then, a sample on the section was washed with PBS, and incubated for 1 hour with corresponding fluorescent conjugated secondary antibodies (Donkey anti-rabbit)(Life Technologies) in 1% BSA. In addition, DAPI (Vector Laboratories) was used for nuclear staining. Here, a control group was subjected to experiments performed under the same conditions, except that no primary antibody was used, and was observed with a confocal microscope (Carl Zeiss). The results are shown in FIG. 6.

Figure 7:
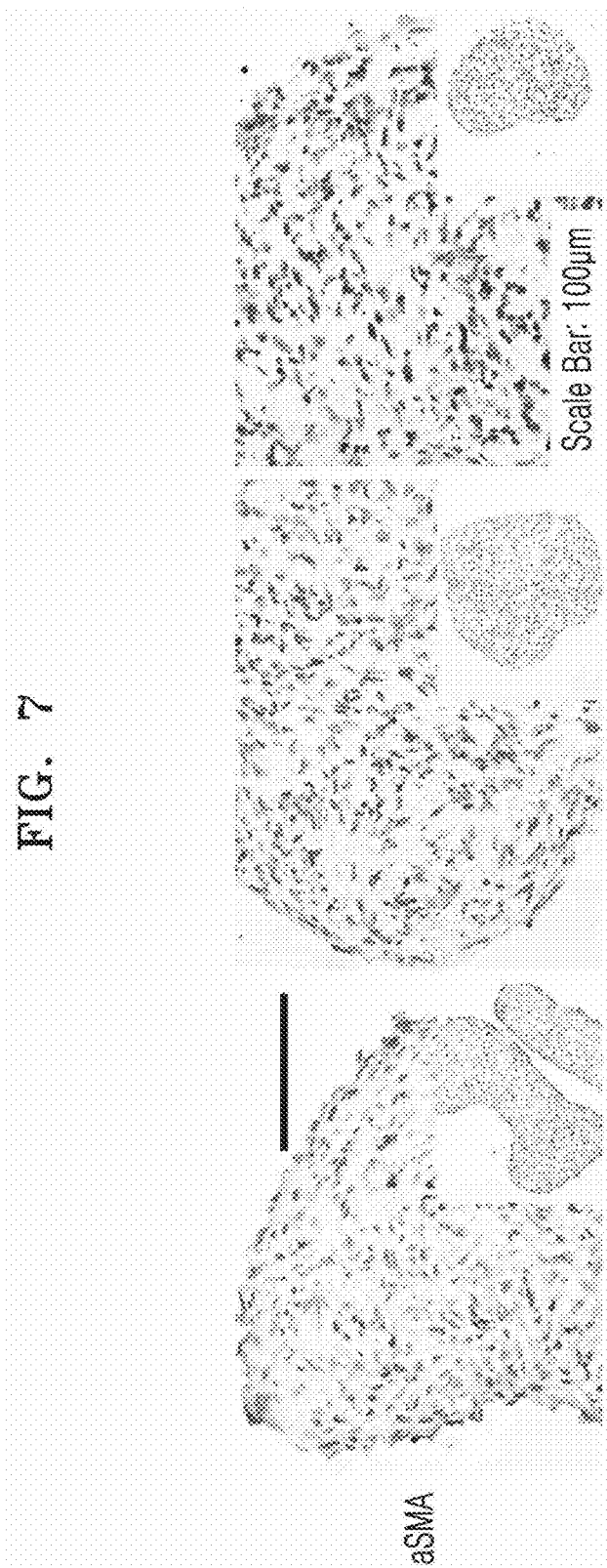
FIG. 7 is a diagram showing results for deposition of collagen type I in a three-dimensional cell cluster according to an embodiment, as identified by immunofluorescence staining.

In addition, for immunohistochemical staining, pretreatment was performed on the 3D cell cluster in the same manner as in H&E staining. Here, fibronectin (FN) and laminin (LN) were each detected by using mouse monoclonal antibodies and goat polyclonal antibodies (Santa cruz Biotechnology) that are specific to FN and LN. In addition, for αSMA analysis, mouse monoclonal antibodies (Dako) were used to detect αSMA. After a section prepared therefrom was incubated overnight at a temperature of 4° C. with primary antibodies for the fibrosis-related factors, the section was incubated at room temperature for 1 hour with horseradish-labeled anti-mouse antibodies (specific to FN and αSMA) and anti-goat secondary antibodies (specific to LN) (Vector). Then, positive staining was visualized using diaminobenzidine (DAB, Vector). Here, a control group was subjected to experiments performed under the same conditions, except that no primary antibody was used. A section obtained therefrom was counter-stained with Haematoxylin and observed with a light microscope, and the results are shown in FIG. 7.

Figure 8:
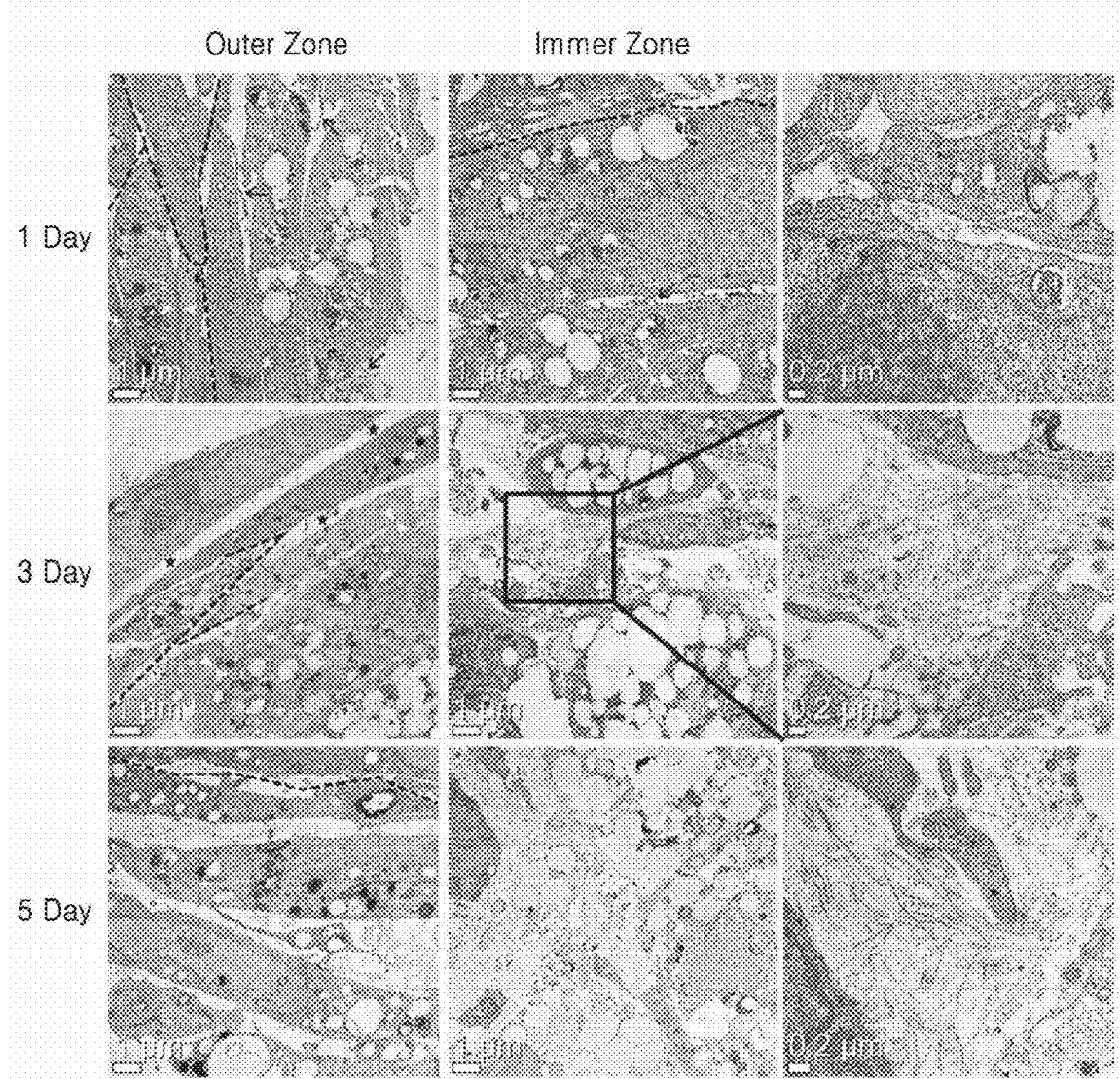
FIG. 8 shows transmission electron microscope (TEM) images of a three-dimensional cell cluster according to an embodiment.

In addition, for transmission electron microscopy (TEM), pretreatment was performed on a sample in the same manner as used for scanning electron microscopy. Additionally, the immobilized 3D cell cluster was infiltrated into an epoxy resin, embedded therein, and polymerized at a temperature of 60° C. for 24 hours. An ultrathin section was prepared by using an ultramicrotome (Ultra cut C, Leica CO. Ltd), and then, was stained with uranyl acetate and lead citrate. TEM images were observed by cryo-TEM (cryoTecanai F20, FEI Co. Ltd), and the results are shown in FIG. 8.

FIGS. 5A and 5B show the results for the deposition of collagen in the 3D cell cluster according to an embodiment, as identified by immunofluorescence staining and analysis of hydroxyproline contents.

FIG. 6 is a diagram showing the results for the deposition of collagen type I in the 3D cell cluster according to an embodiment, as identified by immunofluorescence staining.

FIG. 7 is a diagram showing the results for the deposition of collagen type I in the 3D cell cluster according to an embodiment, as identified by immunofluorescence staining.

FIG. 8 shows TEM images of the 3D cell cluster according to an embodiment.

As shown in FIGS. 5A and 5B, it was confirmed that a majority of collagen was stained in the 3D cell cluster by MT staining and that the content of hydroxyproline was also increased in the 3D cell cluster as compared with that of hydroxyproline in 2D cells.

In addition, as shown in FIG. 6, it was confirmed that collagen type I was significantly increased in the 3D cell cluster, as identified by IF.

In addition, as shown in FIG. 7, it was confirmed that αSMA was significantly increased in the 3D cell cluster, as identified by immunohistochemical staining. αSMA is a traditional marker of myofibroblasts, and collagen type I is known to be synthesized from myofibroblasts in fibrosis. That is, the results above are deemed to be consistent with the results of FIG. 6.

In addition, as shown in FIG. 8, by referring to the TEM images, it was confirmed that the deposition of collagen fibers and collagen gradually increased as the culture time of the 3D cell cluster increased. In detail, thick collagen fibers were observed (see arrows) on Day 5 of the culture, wherein such observation is deemed to be caused by cross-linking of collagen. In addition, on Day 5 of the culture, it was confirmed that no intact cell structure was observed inside the 3D cell cluster. As a result, collagen fibers became thicker around the cells, which caused apoptosis of the cells due to lack of transport of nutrients. Therefore, it was confirmed that the pathological characteristics of fibrosis were modeled by the 3D cell cluster according to an embodiment.

(2.4) Analysis of Viability and Apoptosis of Cells in 3D Cell Cluster Derived from Adipose Stem Cell The deposition of collagen ultimately induced apoptosis of cells in fibrosis. Thus, to confirm that such characteristics appeared in a 3D cell cluster derived from adipose stem cells, an LDH assay and a live/dead assay were performed on the 3D cell cluster.

Figure 9A:
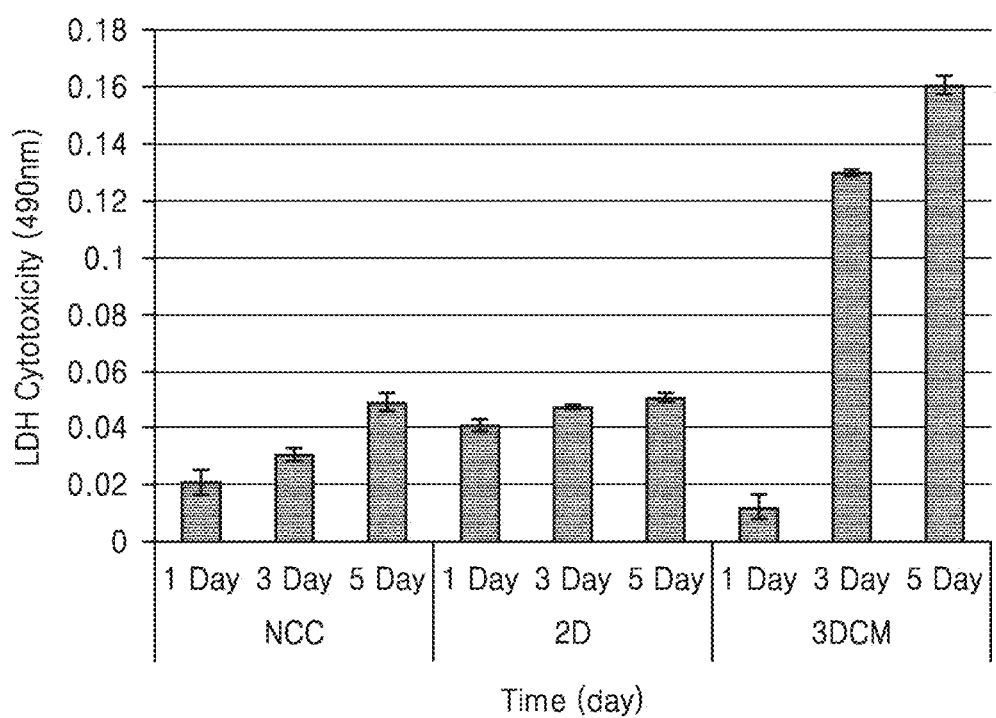
FIG. 9A is a graph showing results for viability and apoptosis of cells in a three-dimensional cell cluster according to an embodiment.

In detail, for the LDH assay, among a culture medium prepared with NCC, 2D cells, and 3D cell cluster, absolute lactic dehydrogenase (LDH) release was measured. The measurement was performed using the LDH assay kit (Promega) according to the manufacturer's instructions. Here, the absorbance was measured using Multiskan (Thermo) at 560 nm, and the results are shown in FIG. 9A. In addition, for the live/dead assay, a live/dead assay kit (Molecular probes) was used according to the manufacturer's instructions. In summary, the collected 3D cell cluster was treated with 1 ml of HEPES-buffered saline (HBSS) containing 1 μl of green-fluorescent nucleic acid staining solution (SYTO 10) and 1 μl of red-fluorescent nucleic acid staining solution (ethidium homodimer-2), and then cultured in a $CO_2$ culture medium for 30 minutes. Afterwards, the resulting 3D cell cluster was washed three times with PBS, immobilized with 4% PFA for 30 minutes, embedded in an OCT compound (TISSUE-TEK® 4583; Sakura Finetek USA, Inc.), and then frozen at a temperature of −28° C. The resulting 3D cell cluster was cut to a thickness of 10 μm. The entire 3D cell cluster was completely cut, and two slides were selected from the middle and outer portions of each sample. Here, the sections were analyzed using a confocal microscope (Carl Zeiss), and the results are shown in FIG. 9B.

Figure 9B:
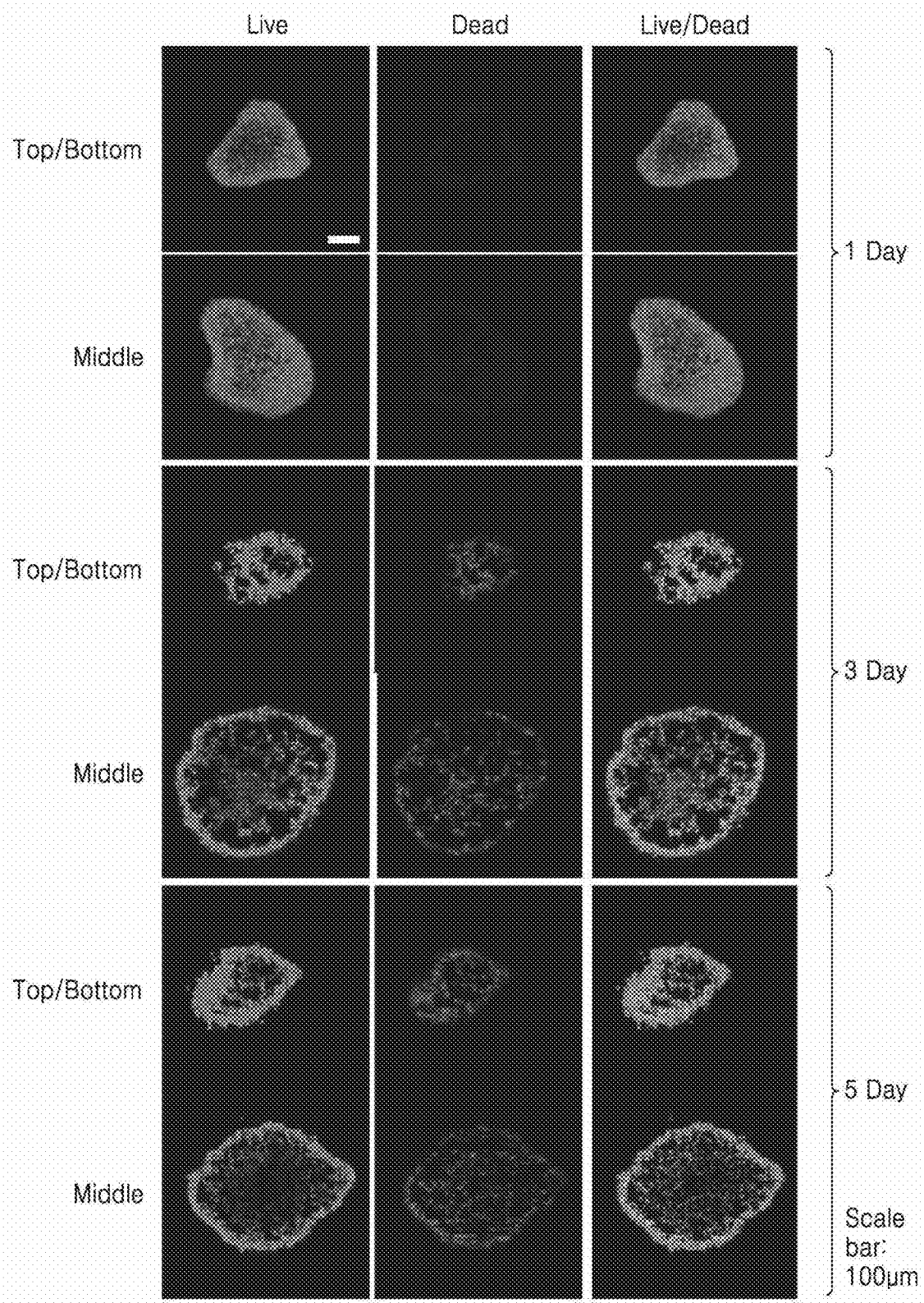
FIG. 9B is a diagram showing results for viability and apoptosis of cells in a three-dimensional cell cluster according to an embodiment.

FIGS. 9A and 9B show the results for viability and apoptosis of cells in the 3D cell cluster according to an embodiment.

As shown in FIG. 9A, according to the LDH assay, the 3D cell cluster showed increased LDH levels as compared with those in NCC and 2D cells. In addition, as shown in FIG. 9B, the apoptosis of cells was visually identified in the 3D cell cluster in the same manner as in FIG. 9A.

As a result, the 3D cell cluster according to an embodiment exhibited pathological characteristics of fibrosis, and thus it was confirmed to be suitable for use as an in vitro fibrosis model.

The invention claimed is:

1. A method of screening a candidate therapeutic agent for treatment of a fibrotic disease, the method comprising:
    culturing adipose stem cells to form a three-dimensional (3D) cell cluster by adhering the adipose stem cells to a culture container comprising a hydrophobic surface, wherein the hydrophobic surface is coated with a growth factor immobilized to the hydrophobic surface through a polypeptide linker, and wherein the growth factor comprises vascular endothelial growth factor (VEGF), fibroblast growth factor (FGF), epidermal growth factor (EGF), platelet-derived endothelial growth factor (PDGF), hepatocyte growth factor (HGF), insulin-like growth factor (IGF), or a heparin-binding domain (HBD), and wherein the polypeptide linker comprises a maltose-binding protein (MBP), a hydrophobin, or a hydrophobic cell penetrating peptide (CPP);
    culturing the 3D cell cluster for 3 days to 10 days to provide an in vitro fibrosis model comprising the 3D cell cluster;
    treating the in vitro fibrosis model comprising the 3D cell cluster with a test substance; and
    selecting, as a candidate therapeutic agent for treatment of the fibrotic disease, a test substance which exhibits improvement or treatment of pathological characteristics of fibrosis in the 3D cell cluster or cells thereof in the in vitro fibrosis model, as compared with an untreated control group.

2. The method of claim 1, wherein the 3D cell cluster is spherical and has a diameter in a range of about 300 μm to about 2,000 μm.

3. The method of claim 1, wherein the pathological characteristics of fibrosis comprise at least one selected from the group consisting of:
- increased deposition of collagen;
- increased expression, secretion, or synthesis of a fibrosis-related molecule including at least one selected from the group consisting of transforming growth factor (TGF)-beta, Smad, laminins, and smooth muscle actin (SMA); and
- increased cell death induced by deposition of collagen, or a combination thereof, in the 3D cell cluster or cells constituting the 3D cell cluster compared to a two-dimensional culture of the adipose stem cells.

4. The method of claim 1, wherein the fibrotic disease comprises at least one selected from the group consisting of idiopathic pulmonary fibrosis (IPF), pulmonary fibrosis, interstitial lung disease, nonspecific interstitial pneumonia (NSIP), usual interstitial pneumonia (UIP), endomyocardial fibrosis, mediastinal fibrosis, bone marrow fibrosis, retroperitoneal fibrosis, progressive massive fibrosis, nephrogenic systemic fibrosis, Crohn's disease, chronic myocardial infarction, scleroderma/systemic sclerosis, neurofibromatosis, Hermansky-Pudlak syndrome, diabetic kidney disease, renal fibrosis, hypertrophic cardiomyopathy (HCM), hypertension-related nephropathy, renal tubulointerstitial fibrosis, focal segmental glomerulosclerosis (FSGS), radiation-induced fibrosis, fibroids, alcoholic liver disease, liver steatosis, liver fibrosis, liver cirrhosis, Hepatitis C Virus (HCV) infection, chronic rejection of transplanted organ, fibrotic skin disease, keloidal scar, Dupuytren's contracture, Ehlers-Danlos syndrome, epidermolysis bullosa dystrophica, oral submucous fibrosis, and fiber proliferative disorder.

\* \* \* \* \*